(12) United States Patent
Takeoka et al.

(10) Patent No.: US 8,900,156 B2
(45) Date of Patent: Dec. 2, 2014

(54) ELECTRONIC SPHYGMOMANOMETER THAT CAN CONFIRM AIR LEAKAGE

(75) Inventors: Kohei Takeoka, Kyoto (JP); Shingo Yamashita, Kyoto (JP)

(73) Assignee: OMRON HEALTHCARE Co., Ltd., Kyoto (JP)

( * ) Notice: Subject to any disclaimer, the term of this patent is extended or adjusted under 35 U.S.C. 154(b) by 220 days.

(21) Appl. No.: 13/155,920

(22) Filed: Jun. 8, 2011

(65) Prior Publication Data

US 2012/0143069 A1 Jun. 7, 2012

Related U.S. Application Data

(63) Continuation of application No. PCT/JP2009/070338, filed on Dec. 3, 2009.

(30) Foreign Application Priority Data

Dec. 9, 2008 (JP) ................................ 2008-313621

(51) Int. Cl.
*A61B 5/02* (2006.01)
*A61B 5/022* (2006.01)
*A61B 5/021* (2006.01)
*G01M 3/32* (2006.01)

(52) U.S. Cl.
CPC ......... *A61B 5/02233* (2013.01); *A61B 5/02141* (2013.01); *G01M 3/32* (2013.01)
USPC ........................................................ 600/490

(58) Field of Classification Search
USPC .................. 600/300, 480, 481, 485–499, 503
See application file for complete search history.

(56) References Cited

U.S. PATENT DOCUMENTS

| 5,025,793 | A  | * | 6/1991 | Richley et al. ................ 600/490 |
| 2004/0127801 | A1 | * | 7/2004 | Takahashi et al. ............ 600/485 |
| 2006/0116588 | A1 |   | 6/2006 | Archibald et al. |
| 2010/0010357 | A1 | * | 1/2010 | Ostrowiecki ................ 600/499 |

FOREIGN PATENT DOCUMENTS

| JP | 2002-078686 A | 3/2002 |
| JP | 2004-160186 A | 6/2004 |
| JP | 2008-241410 A | 10/2008 |

OTHER PUBLICATIONS

Patent Abstracts of Japan, Publication No. 2008-241410, Publication Date: Oct. 9, 2008, 1 page.
Patent Abstracts of Japan, Publication No. 2002-078686, Publication Date: Mar. 19, 2002, 1 page.

(Continued)

*Primary Examiner* — Michael Kahelin
*Assistant Examiner* — Mitchell E Alter
(74) *Attorney, Agent, or Firm* — Osha Liang LLP

(57) ABSTRACT

In an electronic sphygmomanometer, a CPU inlets air into a closed space, including an air bladder in an arm band, an air tube, and another air tube up to a predetermined pressure using a pump, maintains the closed space in a closed state for a certain time, and monitors a decrease in pressure within the maintained time using a pressure sensor. A determination that the air leakage is generated in the closed space including the air bladder and the air tubes is made when the pressure is decreased lower than an allowable amount or more. Similarly, the inspection is also performed to a closed space including the other air tube. The CPU determines whether the air leakage is generated and determines whether an air leakage point exists in the space including the air bladder and the air tube or the space including the other air tube.

6 Claims, 8 Drawing Sheets

(56) References Cited

OTHER PUBLICATIONS

Patent Abstracts of Japan, Publication No. 2004-160186, Publication Date: Jun. 10, 2004, 1 page.

International Search Report issued in PCT/JP2009/070338 mailed on Jan. 19, 2010, and English translation thereof, 4 pages.
Office Action issued in corresponding Russian Application No. 2011128445/14(042083) dated Nov. 1, 2013, and English translation thereof (6 pages).

* cited by examiner

ELECTRONIC SPHYGMOMANOMETER THAT CAN CONFIRM AIR LEAKAGE

TECHNICAL FIELD

The present invention relates to an electronic sphygmomanometer, particularly to an electronic sphygmomanometer that attaches a cuff including a fluid bladder to a measurement region and measures a blood pressure of the measurement region by a change in internal pressure of the fluid bladder.

BACKGROUND ART

When the blood pressure is measured with the electronic sphygmomanometer, an arm band (cuff) in which a fluid bladder such as an air bladder is incorporated is wrapped around an arm or a wrist of a person to be measured, and air is supplied to the arm band to enhance a pressure. In the electronic sphygmomanometer, the pressure of a pulse corresponding to the arm band of the person to be measured is detected as a change in internal pressure of the air bladder, and a blood pressure value is computed based on the change in internal pressure. Therefore, when a phenomenon called an air leakage in which the air leaks from the arm band or an air tube is generated, the pressure of the pulse of the person to be measured cannot be correctly obtained, and the blood pressure value cannot be correctly computed. Because the pressure of the arm band cannot be enhanced, the blood pressure measurement cannot be performed.

As to the technology of confirming the air leakage in the electronic sphygmomanometer, for example, Japanese Unexamined Patent Publication No. 2004-160186 (Patent Document 1) discloses a technology of changing a power supply voltage to switch behavior modes in the electronic sphygmomanometer, and the behavior modes include an air leakage test. In an inspection method of an electronic sphygmomanometer that has been applied by the inventor, a mercury sphygmomanometer, a T-shape tube, and an air tube are prepared, the main body of the electronic sphygmomanometer, the cuff, and the mercury sphygmomanometer are connected through the T-shape tube, and a measurement value of the electronic sphygmomanometer is confirmed by comparing pressure values of the electronic sphygmomanometer and mercury sphygmomanometer.

Patent Document 1: Japanese Unexamined Patent Publication No. 2004-160186

SUMMARY OF INVENTION

However, in the method disclosed in Patent Document 1, it is necessary to perform an operation to change the power supply voltage of the electronic sphygmomanometer. For example, when a user who does not have a special skill handles the electronic sphygmomanometer for a standard home, the user cannot easily inspect the air leakage. The inspection method of the electronic sphygmomanometer that has been applied by the inventor is a method of confirming an error of the pressure in the electronic sphygmomanometer, and the inspection method is not an exact method of detecting the air leakage.

Because a pressure generation device and a pressure detection device are required in performing a general air leakage inspection, a user who does not have the pressure generation device and the pressure detection device cannot inspect the air leakage.

When the user suspects the air leakage may be generated in the electronic sphygmomanometer, even if only the arm band is an exchange target, the user makes a request of the air leakage inspection to a manufacturer, and the air leakage inspection is performed by the manufacturer using the pressure generation device and the pressure detection device to specify an air leakage point. Then a repair is performed or a component is exchanged. Therefore, unfortunately a large amount of time and a large amount of expense are required to eliminate the air leakage. In particular, frequently the user daily uses the sphygmomanometer for the purpose of health management. Therefore, when a large amount of time is required to eliminate the air leakage, a large burden is applied to the user who daily uses the sphygmomanometer.

Therefore, one or more embodiments of the present invention provides an electronic sphygmomanometer that can confirm the generation of the air leakage and the air leakage point by a simple operation.

According to one or more embodiments of the present invention, an electronic sphygmomanometer includes: a pressure sensor that is connected to a closed space to detect an internal pressure of the closed space; a control device that controls inlet and exhaust of a fluid with respect to the closed space; an arithmetic device; and a switching mechanism that switches an area in the closed space connected to the pressure sensor between a first space and a second space, the first space and the second space differing from each other in at least a part. The arithmetic device performs arithmetic processing of computing a blood pressure of a measurement region around which a fluid bladder included in the closed space is wrapped and determination processing of determining whether an air leakage is generated from the closed space based on a change of the internal pressure, the control device controls the switching of the switching mechanism when the arithmetic device further specifies a space including an air leakage point in the determination processing.

According to one or more embodiments of the present invention, the control device stops the inlet and exhaust of the fluid for a specified time after the fluid is inlet into the closed space up to a predetermined pressure when the arithmetic device performs the determination processing, and the arithmetic device determines whether the air leakage is generated from the closed space based on the change of the internal pressure within the specified time in the determination processing.

According to one or more embodiments of the present invention, the first space is a space that includes the fluid bladder, and the second space is a space that does not include the fluid bladder.

According to one or more embodiments of the present invention, the first space is a space including the fluid bladder and all tubes that inlet the fluid into the fluid bladder, and the second space is a space in which the fluid bladder and the tube connected directly to the fluid bladder are removed from the first space.

According to one or more embodiments of the present invention, the control device controls the switching mechanism to switch the first space to the second space when the arithmetic device determines that the air leakage is generated in the first space based on the change of the internal pressure of the first space as a result of the determination processing, the arithmetic device determines whether the air leakage is generated in the first space in the determination processing, the arithmetic device determines whether the air leakage is generated in the second space when the determination that the air leakage is generated in the first space is made, and the arithmetic device specifies whether the air leakage point exists in the space including the fluid bladder and the tube connected directly to the fluid bladder or the space in which the fluid bladder and the tube connected directly to the fluid bladder are removed from the first space from a result of the determination whether the air leakage is generated in the first space and a result of the determination whether the air leakage is generated in the second space.

According to one or more embodiments of the present invention, the electronic sphygmomanometer further includes a storage device in which a date when the determination whether the air leakage is generated is made in the determination processing of the arithmetic device is stored, wherein the control device determines timing in which the arithmetic device performs the determination processing of determining whether the air leakage is generated based on an elapse time since the latest date or the number of measurement times.

According to one or more embodiments of the present invention, even if the user does not have a special device or special skill, the user can specify the generation of the air leakage and the air leakage point by a simple operation. When the air leakage point is specified as the cuff connected to the main body of the electronic sphygmomanometer, the cuff is exchanged without making the request to repair the main body of the electronic sphygmomanometer to the manufacturer, or the defect caused by the air leakage can be eliminated by making the request to exchange the cuff to the manufacturer. Therefore, temporal and economic loads on the user can be suppressed.

DETAILED DESCRIPTION OF INVENTION

Embodiments of the present invention will be described in detail with reference to the drawings. In the following description, the same symbols are denoted for the same components and constituent elements. The names and functions of these components and constituent elements are the same.

Figure 1:
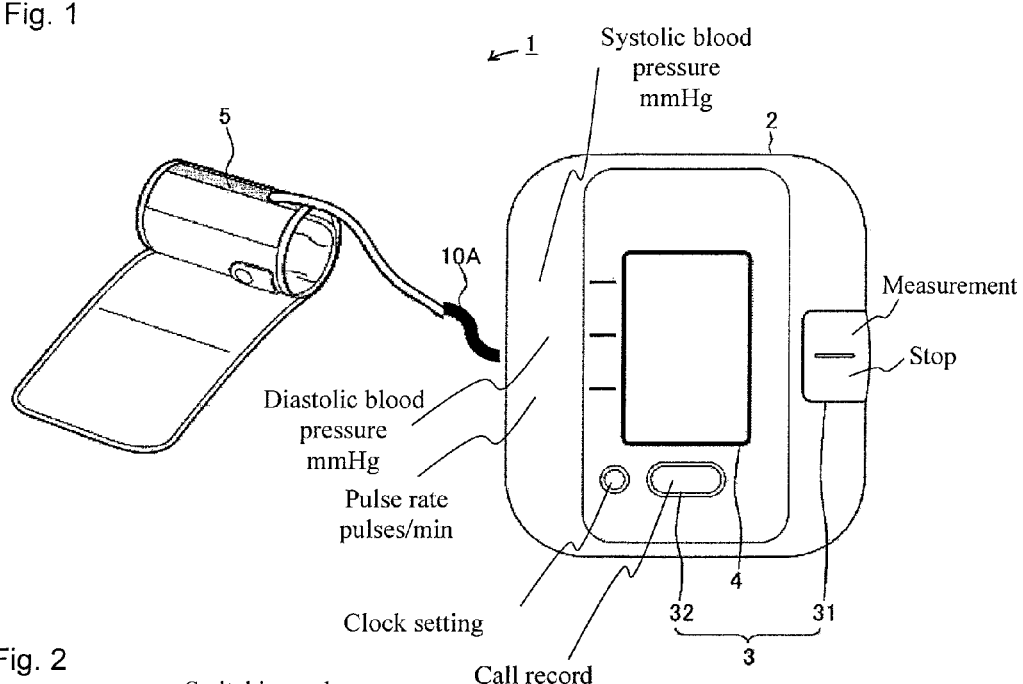
FIG. 1 is a view illustrating a specific example of an appearance of a sphygmomanometer according to an embodiment of the present invention.

Referring to FIG. 1, an electronic sphygmomanometer (hereinafter abbreviated to a sphygmomanometer) 1 according to one or more embodiments of the present invention includes a main body 2 and an arm band 5 that is worn around the upper arm or wrist that is of the measurement region and incorporates an air bladder (not illustrated) therein. The main body 2 and the arm band 5 are connected through an air tube 10A. An operation unit 3 such as a switch and the display unit 4 for displaying the measurement result are arranged on the front surface of the main body 2. The operation unit 3 includes a switch 31 that issues an instruction to turn on and off a power supply and an instruction to start and stop the measurement and a switch 32 that issues an instruction to call and display a recorded measurement value.

Figure 2:
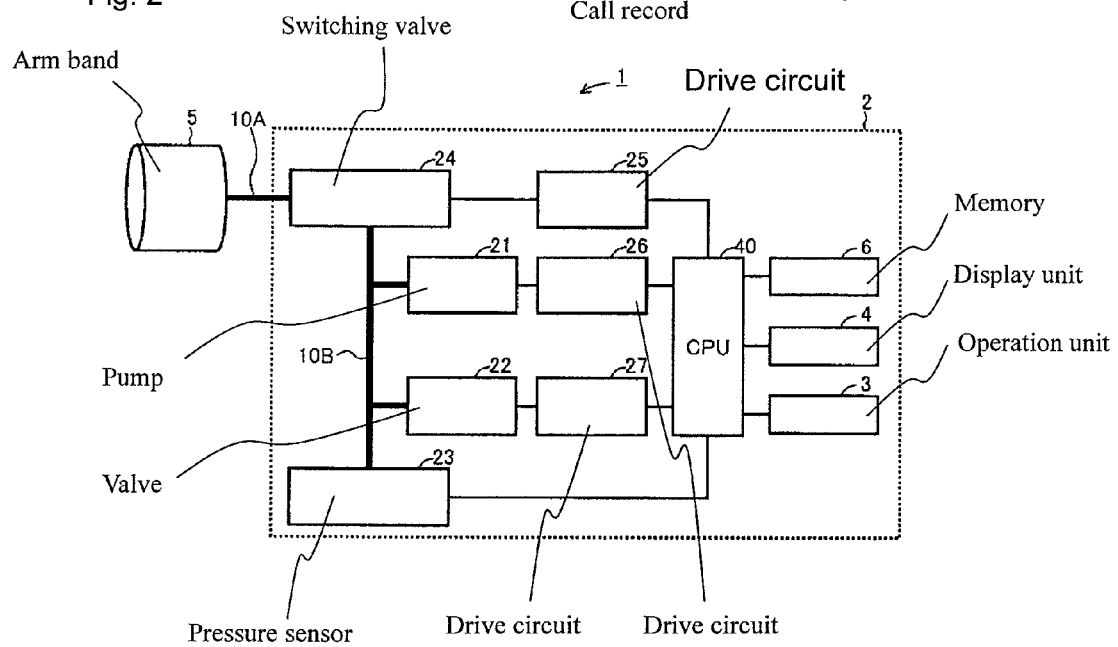
FIG. 2 is a block diagram illustrating a specific example of a hardware configuration of the sphygmomanometer according to an embodiment of the present invention.

Referring to FIG. 2, the arm band 5 is connected to a switching valve 24 through the air tube 10A. The switching valve 24 is also connected to a pump 21, a valve 22, and a pressure sensor 23 through an air tube 10B in the main body 2. The switching valve 24 is connected to a drive circuit 25 and driven by the drive circuit 25, the pump 21 is connected to a drive circuit 26 and driven by the drive circuit 26, and the valve 22 is connected to a drive circuit 27 and driven by the drive circuit 27, respectively. The pressure sensor 23 and the drive circuits 25, 26, and 27 are connected to a CPU 40 (Central Processing Unit). The operation unit 3, the display unit 4, and a memory 6 are also connected to the CPU 40.

As well as the measured blood pressure value, a program to perform a measurement behavior and a program to perform an air leakage inspection behavior are stored as a program executed by the CPU 40 in the memory 6. A result of the air leakage inspection may be stored. The CPU 40 reads the program from the memory 6 according to an operation signal input from the operation unit 3 and executes the program, and the CPU 40 outputs a control signal to the drive circuits 26 and 27. The drive circuit 26 drives the pump 21 according to the control signal, and the drive circuit 27 drives the valve 22 according to the control signal.

The switching valve 24 is a two-port valve, and the switching valve 24 includes a valve on a side of the connection to the air tube 10A and a valve on a side of the connection to the air tube 10B, respectively. The switching valve 24 is driven by the drive circuit 25, and the valve on the side of the connection to the air tube 10A and the valve on the side of the connection to the air tube 10B are respectively opened or closed. The valve 22 is driven and opened or closed by the drive circuit 27.

When both the valves of the switching valve 24 are opened while the valve 22 is closed, a closed space is formed by an air bladder (not illustrated) in the arm band 5 and the air tubes 10A and 10B, and a pressure of the closed space is detected by the pressure sensor 23. Hereinafter, the state in which the closed space is formed by the air bladder (not illustrated) in the arm band 5 and the air tubes 10A and 10B is referred to as a "state 1", and the closed space is referred to as a "closed space 1".

The valve of the switching valve 24 on the side of the connection to the air tube 10B is opened, and the valve of the switching valve 24 on the side of the connection to the air tube 10A and the valve 22 are closed, whereby a closed space is formed by the air tube 10B and a pressure of the closed space is detected by the pressure sensor 23. Hereinafter, the state in which the closed space is formed by the air tube 10B is referred to as a "state 2", and the closed space is referred to as a "closed space 2".

It is said that the closed space 2 is a space where the air bladder (not illustrated) in the arm band 5 and the air tube 10A are separated from the closed space 1. The pump 21 is driven by the drive circuit 26 to inlet the air into the closed space 1 or the closed space 2. The air in the closed space 1 or the closed space 2 is exhausted by opening the valve 22.

The pressure sensor 23 inputs a signal indicating the detected pressure to the CPU 40. The CPU 40 executes the measurement program read from the memory 6, thereby computing the blood pressure value of a person to be measured based on the signal input from the pressure sensor 23. The CPU 40 stores the blood pressure value as a measurement result in a predetermined area of the memory 6. The CPU 40 executes the program to perform the air leakage inspection, thereby determining whether the air leakage is generated using the signal input from the pressure sensor 23. The CPU 40 stores a determination result in a predetermined area of the memory 6.

The sphygmomanometer 1 performs a usual blood pressure measurement behavior according to the blood pressure measurement program and an air leakage inspection behavior according to the program to perform the air leakage inspection.

Figure 3:
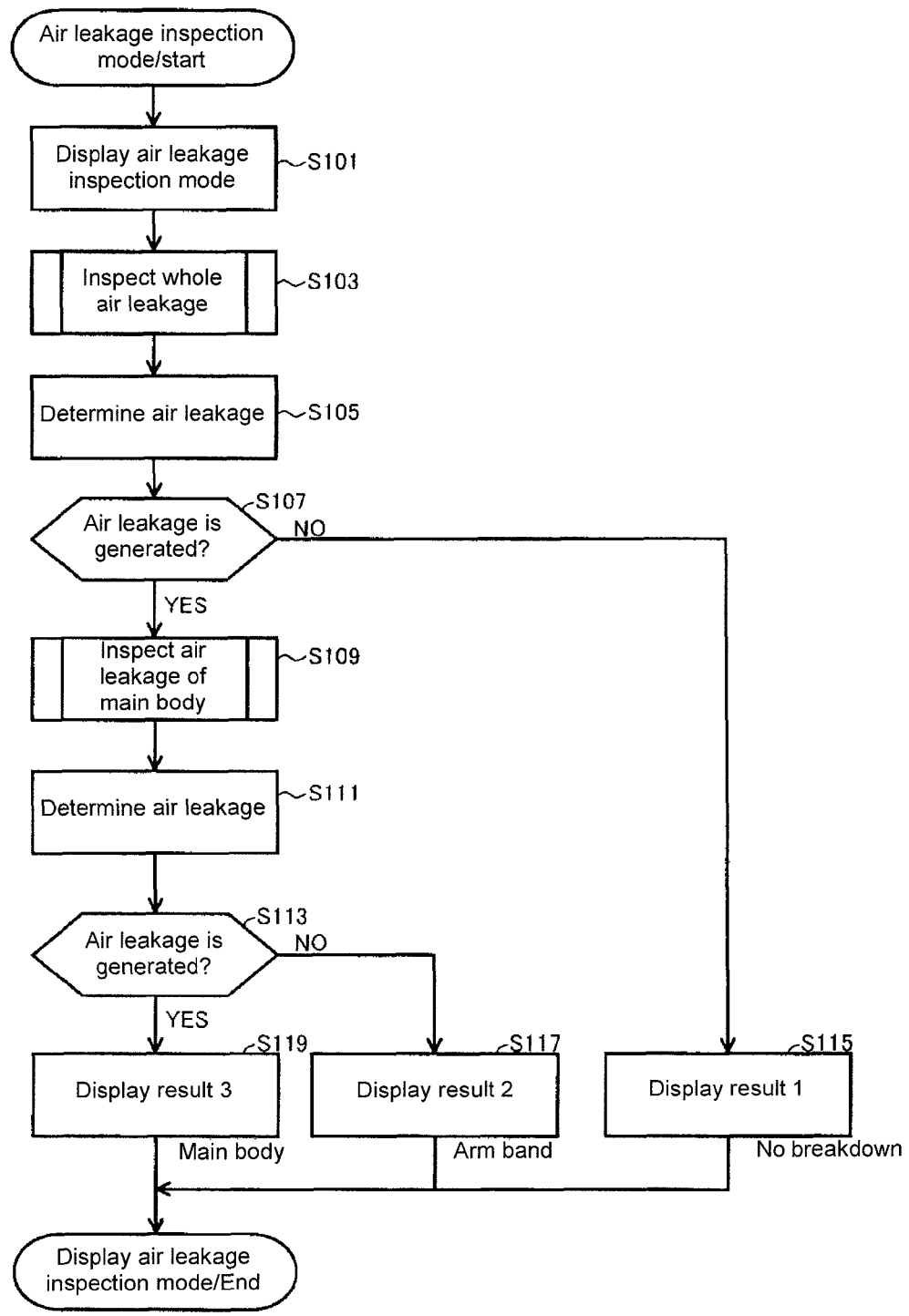
FIG. 3 is a flowchart illustrating a specific example of an air leakage inspection behavior in the sphygmomanometer according to an embodiment of the present invention.

The air leakage inspection behavior of the sphygmomanometer 1 will be described with reference to FIGS. 3 and 4 to 12. The behavior illustrated in the flowchart of FIG. 3 is started by pressing a switch 31 that turns on the power and another switch (switch 32 in FIG. 4). An instruction to start the air leakage inspection behavior may be issued by another operation. When receiving an input of an operation signal associated with the behavior from the operation unit 3, the CPU 40 reads the program to perform the air leakage inspection from the memory 6 and executes the program. Therefore, the behavior illustrated in the flowchart of FIG. 3 is started.

Figure 5:
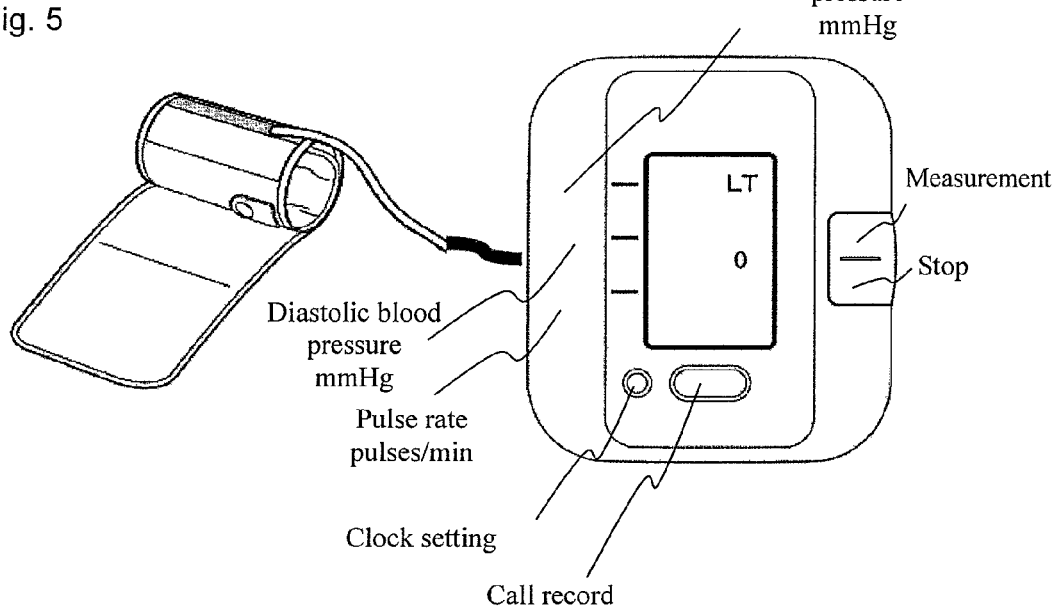
FIG. 5 is a view explaining a sequence of behaviors for air leakage inspection.

When the air leakage inspection behavior is started, in Step S101 the CPU 40 performs previously-stored processing of causing the display unit 4 to display a screen indicating that the air leakage is currently inspected and causes the display unit 4 to perform the display illustrated in FIG. 5. In Step S103, the CPU 40 causes each unit to perform the air leakage inspection behavior according to the program. The air leakage inspection performed in Step S103 is an inspection for the presence or absence of the air leakage in the closed space 1 formed by the air bladder (not illustrated) in the arm band 5 and the air tubes 10A and 10B.

Figure 6:
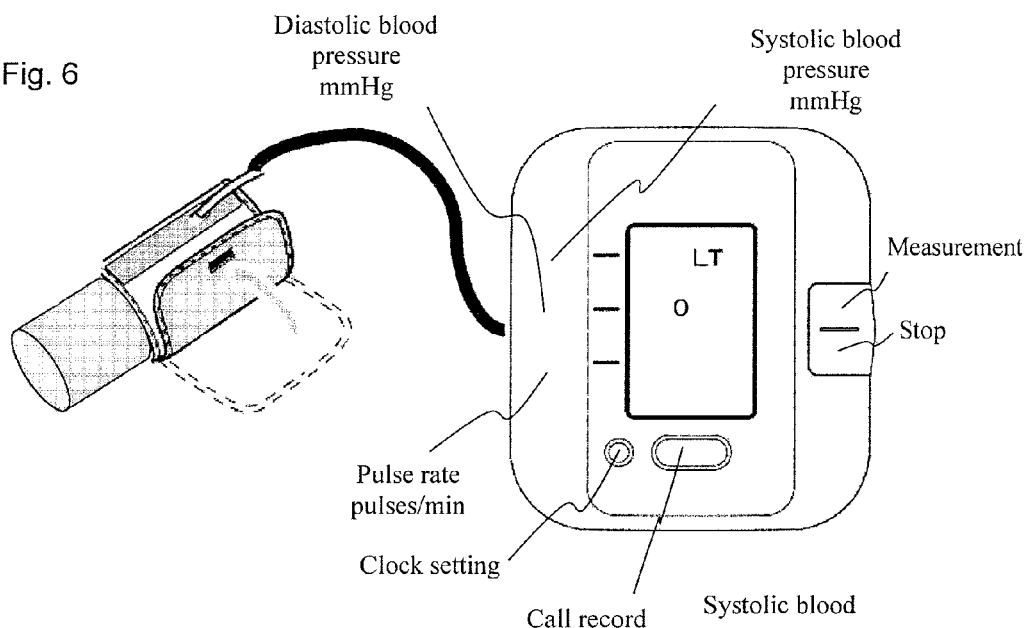
FIG. 6 is a view explaining a sequence of behaviors for air leakage inspection.
Figure 7:
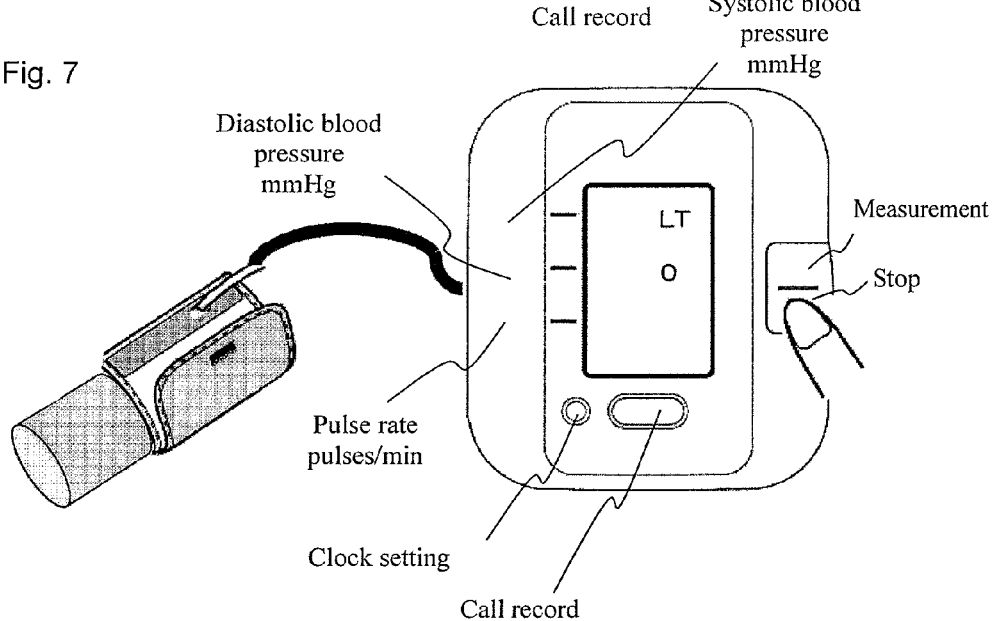
FIG. 7 is a view explaining a sequence of behaviors for air leakage inspection.

In the inspection in Step S103, as illustrated in FIG. 6, an inspection person wraps the arm band 5 around a cylinder having a proper size. When the arm band 5 is wrapped around the cylinder, the switch 31 is pressed to start the measurement as illustrated in FIG. 7. Therefore, when the behavior in Step S103 is started, the CPU 40 executes processing of causing the display unit 4 to display a screen for encouraging the inspection person to wrap the arm band 5 around the cylinder and to press the switch 31, and the CPU 40 causes the display unit 4 to display a notification screen.

During the behavior in Step S103, the CPU 40 opens the valves of the switching valve 24 and outputs the control signal to the drive circuits 25 and 27 to close the valve 22, thereby generating the state 1 to form the closed space 1. When receiving the operation signal indicating that the switch 31 is pressed from the operation unit 3, the CPU 40 outputs the control signal to the drive circuit 26 in order to cause the pump 21 to inlet the air into the closed space 1, thereby increasing the internal pressure of the closed space 1. According to one or more embodiments of the present invention, the CPU 40 performs the air leakage inspection pursuant to a standard relating to the air leakage in JIS standard relating to the sphygmomanometer. Specifically, according to JIS T4203-1990, after the pressure of 200 mmHg is applied to closed space 1 to quietly leave the closed space 1 for 3 minutes, the determination that the air leakage is not generated is made by confirming that the pressure does not drop by 2 mmHg or more.

Figure 8:
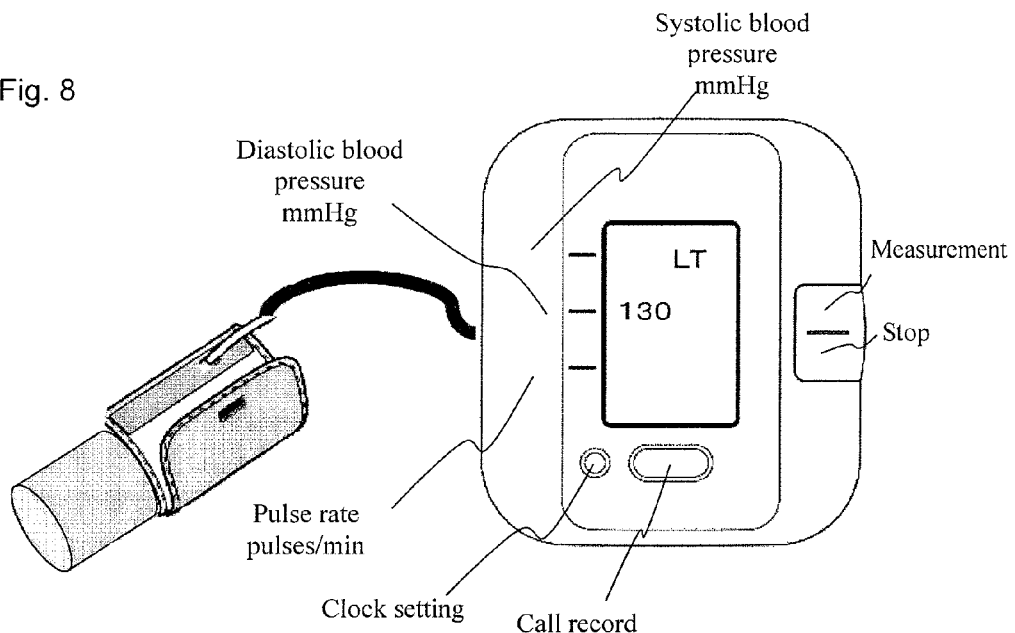
FIG. 8 is a view explaining a sequence of behaviors for air leakage inspection.
Figure 9:
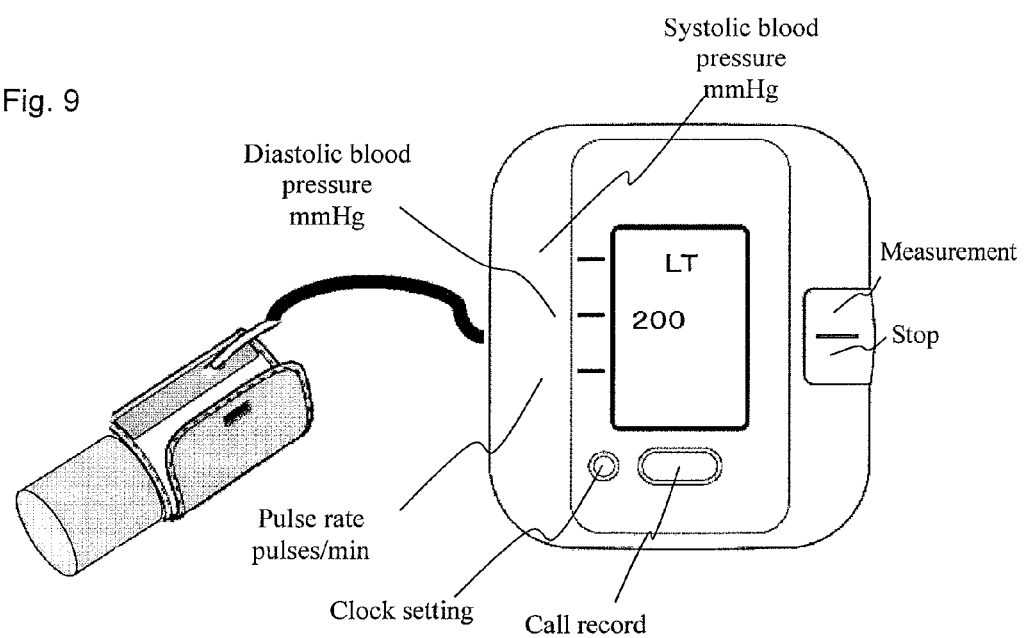
FIG. 9 is a view explaining a sequence of behaviors for air leakage inspection.

When receiving the operation signal indicating that the switch 31 is pressed from the operation unit 3, the CPU 40 causes the pump 21 to inlet the air into the closed space 1 to pressurize the closed space 1 until the internal pressure becomes 200 mmHg. At this point, according to one or more embodiments of the present invention, the CPU 40 detects the pressure in the closed space 1 at predetermined intervals during the pressurization based on the signal from the pressure sensor 23, and the CPU 40 displays the pressure on the display unit 4 as illustrated in FIG. 8. As illustrated in FIG. 9, when the internal pressure of the closed space 1 reaches 200 mmHg, the CPU 40 outputs the control signal to the drive circuit 26 to stop the drive of the pump 21, and starts the timing with a timer (not illustrated). When 3 minutes elapse since the pump 21 is closed, the CPU 40 detects the internal pressure of the closed space 1 based on the signal from the pressure sensor 23, and the CPU 40 determines whether the air leakage is generated in Step S105 while displaying the internal pressure on the display unit 4.

Figure 10:
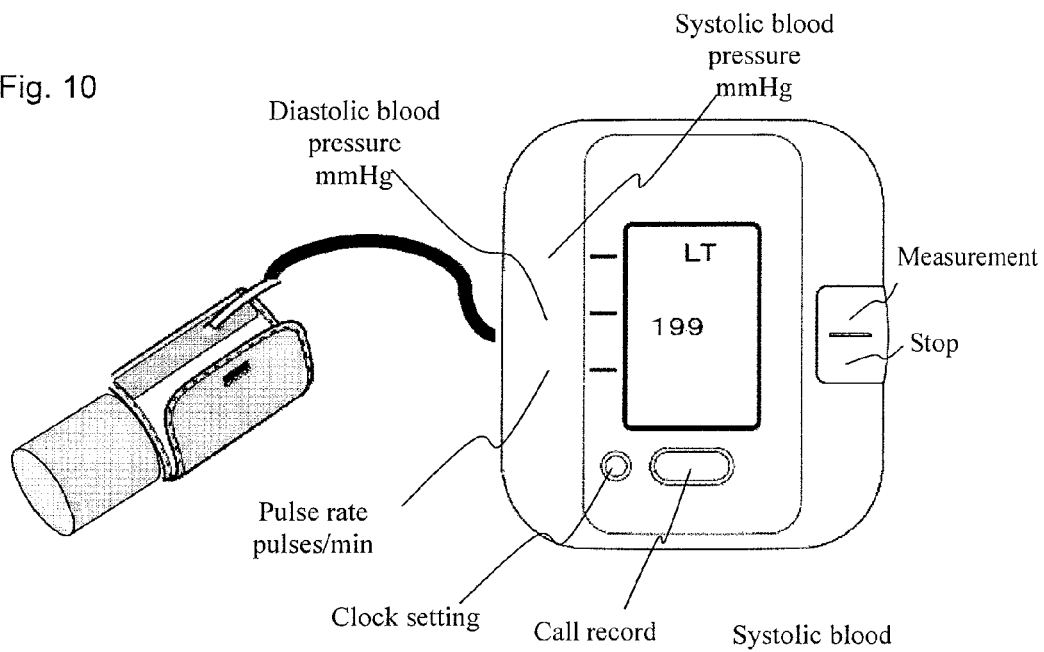
FIG. 10 is a view explaining a sequence of behaviors for air leakage inspection.
Figure 11:
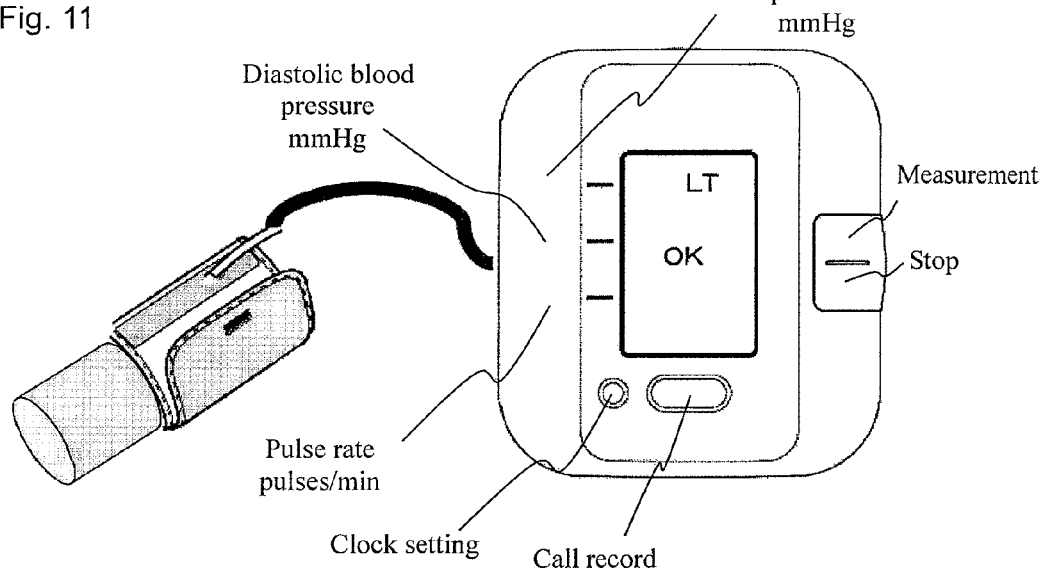
FIG. 11 is a view explaining a sequence of behaviors for air leakage inspection.

As illustrated in FIG. 10, when the internal pressure of 200 mmHg of the closed space 1 is decreased by less than 2 mmHg after 3 minutes elapse since the pump 21 is closed, the CPU 40 determines that the air leakage is not generated in the closed space 1 (NO in Step S107). In Step S115, the CPU 40 determines the air leakage inspection as a "result 1", performs previously-stored processing of causing the display unit 4 to display a screen indicating that the air leakage is not generated, and causes the display unit 4 to display the screen illustrated in FIG. 11. Then the sequence of behaviors is ended.

Figure 12:
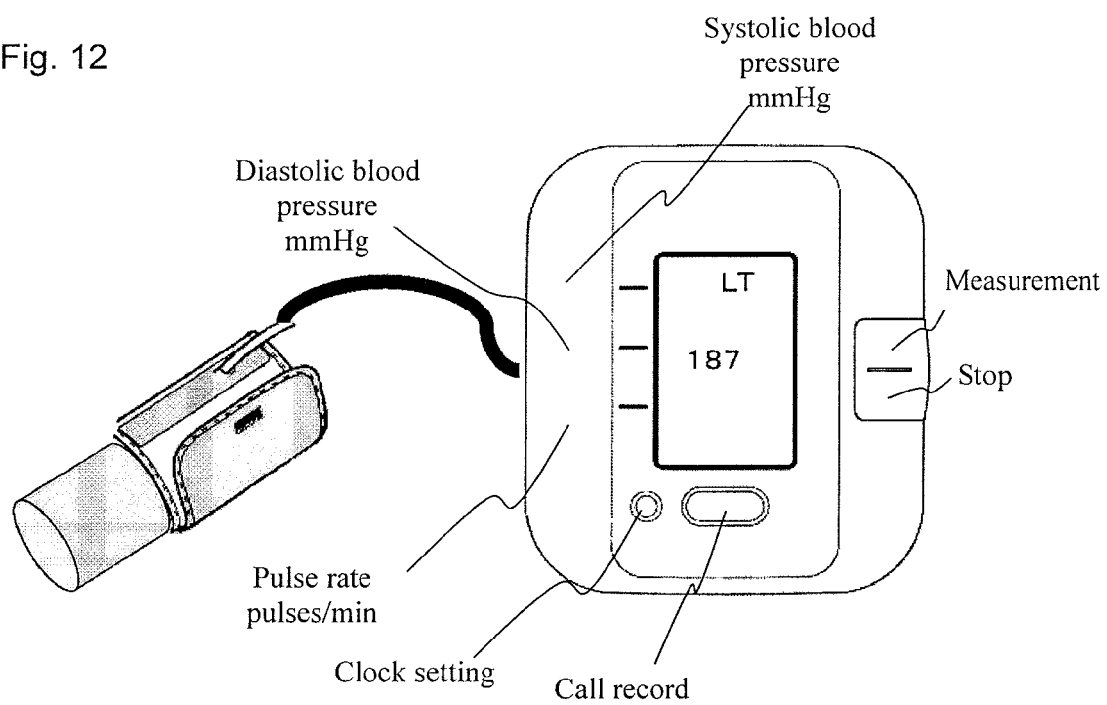
FIG. 12 is a view explaining a sequence of behaviors for air leakage inspection.

As illustrated in FIG. 12, when the internal pressure of 200 mmHg of the closed space 1 is decreased by more than 2 mmHg after 3 minutes elapse since the pump 21 is closed, the CPU 40 determines that the air leakage is generated in the closed space 1 (YES in Step S107), and the flow goes to a behavior in Step S109.

When the behavior in Step S109 is started, the CPU 40 outputs the control signal to the drive circuit 25 to close the valve of the switching valve 24 on the side of the connection to the air tube 10A. Therefore, the state 1 is transferred to the state 2, and the air bladder (not illustrated) in the arm band 5 and the air tube 10A are separated from the closed space 1 to form the closed space 2. When the closed space 2 is formed, similar to the behavior in Step S103, the CPU 40 pressurizes the closed space 2 until the internal pressure reaches 200 mmHg. Then the CPU 40 detects the internal pressure of the closed space 2 based on the signal from the pressure sensor 23 after 3 minutes elapse, thereby making an air leakage determination in Step S111. The air leakage determination in Step S111 is similar to that in Step S105.

As illustrated in FIG. 10, when the internal pressure of 200 mmHg of the closed space 1 is decreased by less than 2 mmHg after 3 minutes elapse since the drive of the pump 21 is stopped, the CPU 40 determines that the air leakage is generated in the closed space 1 and that the air leakage is not generated in the closed space 2 (NO in Step S113). In Step S117, the CPU 40 performs processing of causing the display unit 4 to display a screen indicating a "result 2" and causes the display unit 4 to display the screen indicating the "result 2".

As illustrated in FIG. 12, when the internal pressure of 200 mmHg of the closed space 1 is decreased by more than 2 mmHg after 3 minutes elapse since the pump 21 is closed, the CPU 40 determines that the air leakage is generated in the closed space 1 and that the air leakage is also generated in the closed space 2 (YES in Step S113). In Step S119, the CPU 40 performs processing of causing the display unit 4 to display a screen indicating a "result 3" and causes the display unit 4 to display the screen indicating the "result 3".

When the air leakage is not generated in the closed space 1, namely, the whole space formed by the air bladder (not illustrated) in the arm band 5 and the air tubes 10A and 10B (NO in Step S107), the determination that the air leakage point does not exist in the air bladder (not illustrated) in the arm band 5 and the portion that is of the air tube 10A connected to the main body 2 and in the inside of the main body 2 that is of the air tube 10B is made. Accordingly, the "result 1" indicates that the air leakage point does not exist in both the inside of the main body 2 and the connected portion.

Figure 13:
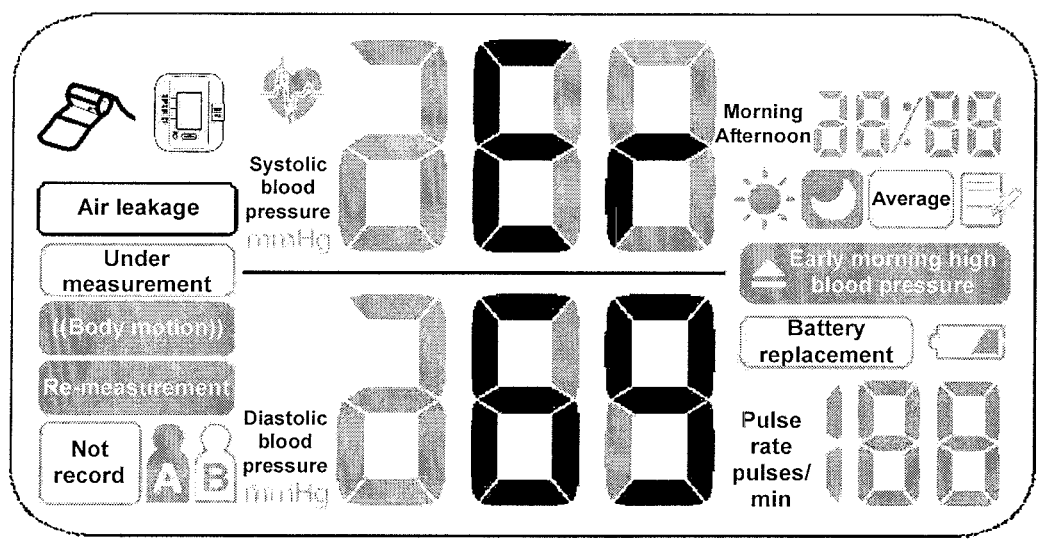
FIG. 13 illustrates a screen example in which result of the air leakage inspection is displayed.

When the air leakage is generated in the closed space 1, namely, the whole space formed by the air bladder (not illustrated) in the arm band 5 and the air tubes 10A and 10B, and when the air leakage is not generated in the closed space 2, namely, the closed space formed by the air tube 10B (NO in Step S113), the determination that the air leakage point does not exist in the inside of the main body 2 that is of the air tube 10B is made, and the determination that the air leakage point exists in the air bladder (not illustrated) in the arm band 5 and the portion that is of the air tube 10A connected to the main body 2 is made. Accordingly, the "result 2" indicates that the air leakage point exists in the portion connected to the main body 2. Therefore, in Step S117, according to one or more embodiments of the present invention, the CPU 40 causes the display unit 4 to display a screen indicating that the air leakage point exists in the portion such as the arm band 5 which is connected to the main body 2 as illustrated in FIG. 13.

When the air leakage is generated in the closed space 1, namely, the whole space formed by the air bladder (not illustrated) in the arm band 5 and the air tubes 10A and 10B, and when the air leakage is generated in the closed space 2, namely, the closed space formed by the air tube 10B (YES in Step S113), the determination whether the air leakage point exists in the air bladder (not illustrated) in the arm band 5 and the portion that is of the air tube 10A connected to the main body 2 is not made, but at least the determination that the air leakage point exists in the inside of the main body 2 that is of the air tube 10B is made. Accordingly, the "result 3" indicates that the air leakage point exists at least in the inside of the main body 2. Therefore, in Step S119, according to one or more embodiments of the present invention, the CPU 40 causes the display unit 4 to display a screen indicating that the air leakage point exists in the inside of the main body 2 similar to the screen illustrated in FIG. 13.

The sphygmomanometer 1 performs the air leakage inspection behavior, so that the user can perform the air leakage inspection by a simple operation even if a special inspection device is not included. The determination that the air leakage point exists in the portion such as the arm band 5 which is connected to the main body 2 is made by the behavior. Therefore, it is not necessary to pass the sphygmomanometer 1 to a manufacturer in order to make a request for the repair or inspection, but the air leakage is eliminated by purchasing or exchanging the portion such as the arm band 5 which is connected to the main body 2. Therefore, the inconvenience that the sphygmomanometer 1 is not used for a long time can be prevented.

Figure 4:
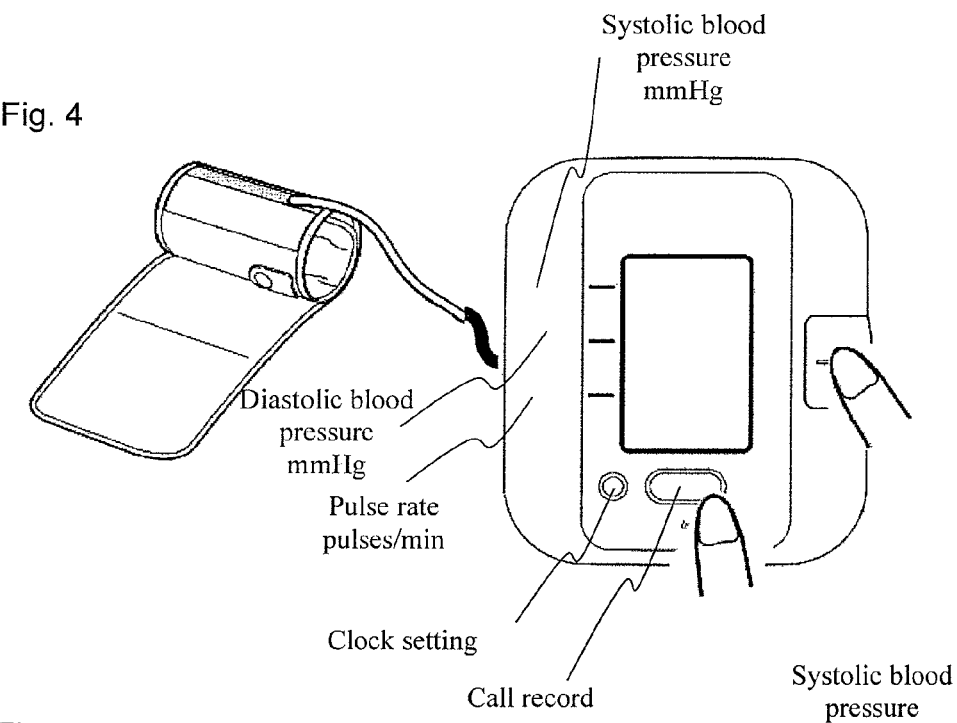
FIG. 4 is a view explaining a sequence of behaviors for air leakage inspection.

According to one or more embodiments of the present invention, the air leakage inspection is performed in the sphygmomanometer 1 by the specific operation as illustrated in FIG. 4. However, in the sphygmomanometer 1, the air leakage inspection behavior may be automatically performed at a predetermined timing. Alternatively, a determination whether the air leakage inspection is required is made at a predetermined timing, and the display encouraging the user to perform the air leakage inspection may be displayed on the display unit 4 when the determination that the air leakage inspection is required is made. In such cases, specific configuration and behavior will be described in the following modifications 1, 2, and 3.

(First Modification)

A sphygmomanometer 1 according to a first modification of the embodiment has a calendar function. When the air leakage inspection behavior is performed, a CPU 40 stores the result (the "result 1", the "result 2", or the "result 3") in a predetermined area of a memory 6 while a date in which the behavior is performed is correlated with the result. The CPU 40 confirms the air leakage inspection result stored in the memory 6 in predetermined timing and determines whether the air leakage inspection behavior is performed from the air leakage inspection result. Timing in which a switch 31 that turns on the power is pressed to perform the usual blood pressure measurement can be cited as an example of the predetermined timing. The predetermined timing may be set after the sequence of blood pressure measurement behaviors.

Examples of the determination whether the air leakage inspection behavior is performed include the case in which some days of a standard elapse since the latest date of the air leakage inspection and the case in which the measurement is performed plural times of a standard. The plural "some days of the standard" are stored according to the latest air leakage inspection result and used according to the air leakage inspection result. Specifically, the "some days of the standard" that is longer than the "some days of the standard" in the case where the air leakage is not generated (the "result 1") can be used when the result that the air leakage is generated (the "result 2" or the "result 3") is obtained in the latest air leakage inspection. This is, it is conceivable that the air leakage point is repaired by making the determination that the air leakage is generated (the "result 2" or the "result 3") in the previous air leakage inspection. Therefore, compared with the case in which the air leakage is not generated, it is not necessary to perform the air leakage inspection at short intervals. The same holds true for the measurement times of the standard.

(Second Modification)

In a second modification, when a portion such as an arm band 5, which is connected to a main body 2 or an air tube 10B in the main body 2, is repaired or exchanged, a CPU 40 stores information indicating the repair or exchange in a predetermined area of a memory 6 while a date in which the repair or exchange is performed is correlated with the information. The CPU 40 can detect that the repair or exchange is performed by receiving a predetermined operation from an operation unit 3. For example, a storage medium such as an IC chip in which information identifying the air tubes 10A and 10B is stored is provided in connection portions of the air tubes 10A and 10B. In such cases, the connection portion includes a read mechanism for the storage medium, and the CPU 40 can detect the exchange based on the identification information read from the storage medium.

The CPU 40 confirms the information indicating that the repair or exchange is performed, which is stored in the memory 6, and determines that the air leakage inspection behavior is performed when the some days of the standard elapse since the previous date of the repair or exchange. Timing in which a switch 31 that turns on the power is pressed to perform the usual blood pressure measurement can be cited as an example of the predetermined timing. The predetermined timing may be set after the sequence of blood pressure measurement behaviors.

(Third Modification)

In a third modification, a CPU 40 stores the blood pressure measurement result in a predetermined area of a memory 6 while the result is correlated with the measurement date. The CPU 40 confirms the measurement result stored in the memory 6 in predetermined timing and determines that the air leakage inspection behavior is performed when the some days of the standard elapse since the previous measurement date.

Similar to the second modification, when a portion such as an arm band 5, which is connected to a main body 2 or an air tube 10B in the main body 2, is repaired or exchanged, the CPU 40 stores the information indicating that a portion such as an arm band 5, which is connected to a main body 2 or an air tube 10B in the main body 2, is repaired or exchanged in a predetermined area of the memory 6 while a date in which the repair or exchange is performed is correlated with the information. The CPU 40 confirms the information indicating that the repair or exchange is performed and the measurement result, which are stored in the memory 6, in predetermined timing and determines that the air leakage inspection behavior is performed when the measurement is performed specified times since the previous date of the repair or exchange.

According to the sphygmomanometers 1 of the first to third modifications, the air leakage inspection is performed at proper timing, and the repair or exchange can quickly be performed when the air leakage point exists. Therefore, the measurement result can be obtained with high accuracy. When the result that the air leakage is generated is obtained in the final air leakage inspection, the blood pressure measurement cannot be started, which allows reliability of the measurement result to be enhanced.

While the invention has been described with respect to a limited number of embodiments, those skilled in the art, having benefit of this disclosure, will appreciate that other embodiments can be devised which do not depart from the scope of the invention as disclosed herein. Accordingly, the scope of the invention should be limited only by the attached claims.

Description Of Reference Numerals

1: sphygmomanometer, 2: main body, 3: operation unit, 4: display unit, 5: arm band, 6: memory, 10A,10B: air tube, 21: pump, 22: valve, 23: pressure sensor, 24: switching valve, 25, 26, 27: drive circuit, 31,32: switch, 40: CPU

The invention claimed is:

1. An electronic sphygmomanometer comprising:
   a pressure sensor that is connected to a closed space to detect an internal pressure of the closed space;
   a control device that controls inlet and exhaust of a fluid with respect to the closed space;
   an arithmetic device; and
   a switching mechanism that switches an area in the closed space connected to the pressure sensor between a first space and a second space,
      wherein the closed space comprises the first space and the second space,
      wherein the first space comprises an air bladder and a first air tube connected from the air bladder to the switching mechanism and a second air tube connected from the switching mechanism to the pressure sensor,
      wherein the second space is contained within the first space,
      wherein the second space is a space where the air bladder and the first air tube are separated from the first space,
      wherein the arithmetic device performs arithmetic processing of computing a blood pressure of a measurement region around which a fluid bladder included in the closed space is wrapped and determination processing of determining whether an air leakage is generated from the closed space based on a change of the internal pressure,
      wherein the control device controls the switching of the switching mechanism when the arithmetic device performs the determination processing, and
      wherein the arithmetic device further specifies a space comprising an air leakage point in the determination processing.

2. The electronic sphygmomanometer according to claim 1,
   wherein the control device stops the inlet and exhaust of the fluid for a specified time after the fluid is inlet into the closed space up to a predetermined pressure when the arithmetic device performs the determination processing, and
   wherein the arithmetic device determines whether the air leakage is generated from the closed space based on the change of the internal pressure within the specified time in the determination processing.

3. The electronic sphygmomanometer according to claim 1,
   wherein the first space is a space that comprises the fluid bladder and the second space is a space that does not comprise the fluid bladder.

4. The electronic sphygmomanometer according to claim 3,
   wherein the first space further comprises a plurality of tubes that inlet the fluid into the fluid bladder, and
   wherein the second space is the space in which the fluid bladder and a tube connected directly to the fluid bladder are removed from the first space.

5. The electronic sphygmomanometer according to claim 4,
   wherein the control device controls the switching mechanism to switch the first space to the second space when the arithmetic device determines that the air leakage is generated in the first space based on the change of the internal pressure of the first space as a result of the determination processing,
   wherein the arithmetic device determines whether the air leakage is generated in the first space in the determination processing,
   wherein the arithmetic device determines whether the air leakage is generated in the second space when the determination that the air leakage is generated in the first space is made, and
   wherein the arithmetic device specifies whether the air leakage point exists in the space comprising the fluid bladder and the tube connected directly to the fluid bladder or the space in which the fluid bladder and the tube connected directly to the fluid bladder are removed from the first space from a result of the determination whether the air leakage is generated in the first space and a result of the determination whether the air leakage is generated in the second space.

6. The electronic sphygmomanometer according to claim 1, further comprising:
   a storage device in which a date when the determination whether the air leakage is generated is made in the determination processing of the arithmetic device is stored,
   wherein the control device determines timing in which the arithmetic device performs the determination processing of determining whether the air leakage is generated based on an elapse time since the latest date or a number of measurement times.

* * * * *